(12) United States Patent
Selbig et al.

(10) Patent No.: US 8,286,512 B1
(45) Date of Patent: Oct. 16, 2012

(54) APPARATUS TO ASSIST IN THE COLLECTION OF STORMWATER-QUALITY SAMPLES IN A VERTICAL PROFILE

(75) Inventors: William R. Selbig, Madison, WI (US); Peter E. Hughes, Madison, WI (US)

(73) Assignee: The United States of America, as represented by the Secretary of the Interior, Washington, DC (US)

(*) Notice: Subject to any disclaimer, the term of this patent is extended or adjusted under 35 U.S.C. 154(b) by 338 days.

(21) Appl. No.: 12/779,549

(22) Filed: May 13, 2010

Related U.S. Application Data

(60) Provisional application No. 61/179,052, filed on May 18, 2009.

(51) Int. Cl.
*G01N 1/20* (2006.01)
(52) U.S. Cl. ........... 73/863.44; 73/863.41; 73/863.51; 73/863.54; 73/863.82; 73/864.81
(58) Field of Classification Search .......... 73/863.41, 73/863.43, 863.51, 863.53, 863.54, 863.58, 73/863.82, 864, 864.31, 864.81
See application file for complete search history.

(56) References Cited

U.S. PATENT DOCUMENTS

| | | | | |
|---|---|---|---|---|
| 2,926,527 A * | 3/1960 | Crandall | ................... | 73/863.58 |
| 2,958,222 A * | 11/1960 | Morgan | ................... | 73/864.31 |
| 2,972,254 A * | 2/1961 | Lambert | ................... | 73/864 |
| 3,789,671 A * | 2/1974 | Larson | ................... | 73/864.32 |
| 3,830,480 A * | 8/1974 | Grant | ................... | 266/99 |
| 3,929,017 A * | 12/1975 | Kowalski | ................... | 73/198 |
| 3,940,993 A * | 3/1976 | Lapidot | ................... | 73/863.02 |
| 3,962,922 A * | 6/1976 | Takeuchi | ................... | 73/864.32 |
| 4,022,059 A * | 5/1977 | Schontzler et al. | ................... | 73/198 |
| 4,037,476 A * | 7/1977 | McCrabb | ................... | 73/864.31 |
| 4,088,025 A * | 5/1978 | Foster et al. | ................... | 73/863.33 |
| 4,295,801 A * | 10/1981 | Bennett | ................... | 417/397 |
| 4,660,422 A | 4/1987 | Eads et al. | | |
| 4,762,009 A * | 8/1988 | Scrudto | ................... | 73/863.52 |
| 4,958,528 A * | 9/1990 | Garrison | ................... | 73/864.63 |
| 5,186,052 A * | 2/1993 | Gray | ................... | 73/215 |

(Continued)

OTHER PUBLICATIONS

Bent, G.C., Gray, J.R., Smith, K.P., and Glysson, G.D., 2000, A synopsis of technical issues for monitoring sediment in highway and urban runoff: U.S. Geological Survey Open-File Report 00-497, 51 p. <http://pubs.usgs.gov/of/2000/ofr00-497/pdf/ofr00497.pdf>.

(Continued)

*Primary Examiner* — David Rogers
(74) *Attorney, Agent, or Firm* — C. Joan Gilsdorf

(57) ABSTRACT

A sampling method, fluid collection assembly, and auxiliary sampling device to assist an autosampler in collecting samples from a fluid source. The auxiliary sampling device includes a support frame with a pivot member. A linear actuator having a piston is attached to the support frame. A rotatable sample arm assembly has an upper end attached to the piston and to the pivot member of the support frame, and a lower end with an inlet to receive a fluid sample. A fluid conduit within the sample arm assembly has a fluid intake end connected to the inlet and a fluid discharge end connected to the autosampler. The linear actuator pushes or retracts the piston to vertically pivot the sample arm assembly until the inlet reaches desired positions within the fluid source so that the autosampler collects multiple samples at various depths.

23 Claims, 8 Drawing Sheets

U.S. PATENT DOCUMENTS

| | | | | |
|---|---|---|---|---|
| 5,211,062 | A | * | 5/1993 | Moser .......................... 73/864.33 |
| 5,279,151 | A | * | 1/1994 | Coody et al. ......................... 73/86 |
| 5,299,141 | A | * | 3/1994 | Hungerford et al. ............. 702/49 |
| 5,347,877 | A | * | 9/1994 | Gadbois ...................... 73/863.52 |
| 5,435,399 | A | * | 7/1995 | Peterson et al. ................. 175/20 |
| 5,463,909 | A | | 11/1995 | Eldridge |
| 5,587,539 | A | * | 12/1996 | Carpenter ................... 73/863.52 |
| 5,606,138 | A | * | 2/1997 | Saarenketo ................. 73/864.34 |
| 5,652,397 | A | * | 7/1997 | Dawson et al. ............ 73/863.61 |
| 5,693,894 | A | * | 12/1997 | Jobson ........................ 73/863.03 |
| RE35,824 | E | * | 6/1998 | Welker ........................ 73/863.83 |
| 5,783,758 | A | | 7/1998 | Dudley |
| 5,811,696 | A | * | 9/1998 | Jobson ........................ 73/863.03 |
| 5,844,148 | A | * | 12/1998 | Klein et al. ................. 73/863.82 |
| 6,742,404 | B2 | | 6/2004 | Smith et al. |
| 7,377,189 | B2 | * | 5/2008 | Champseix et al. ....... 73/864.25 |

OTHER PUBLICATIONS

Smith, K.P., 2002, Effectiveness of three best management practices for highway-runoff quality along the southeast expressway, Boston, Massachusetts: U.S. Geological Survey Water-Resources Investigations Report 02-4059, 62 p. <http://pubs.usgs.gov/wri/wri024059/pdfs/wri024059.pdf>.

Kayhanian, M., Young, T., and Stenstrom, M., 2005, Limitation of current solids measurements in stormwater runoff, Stormwater, v. 6, No. 5, p. 40-58. <http://www.stormh2o.com/july-august-2005/solids-measurements-runoffaspx>.

DeGroot, G.P., Gulliver, J.S., and Mohseni, O., 2009, Accurate sampling of suspended solids, ASCE Conf. Proc. 342, 81 (2009).

* cited by examiner

APPARATUS TO ASSIST IN THE COLLECTION OF STORMWATER-QUALITY SAMPLES IN A VERTICAL PROFILE

CROSS-REFERENCE TO RELATED APPLICATION(S)

This application is related to and claims the benefit of priority to Provisional Application U.S. Ser. No. 61/179,052, entitled "Apparatus to Assist in the Collection of Stormwater-Quality Samples in a Vertical Profile," by Selbig et al., filed May 18, 2009 in the U.S. Patent and Trademark Office, the contents of which are incorporated herein by reference.

STATEMENT OF GOVERNMENT INTEREST

The invention described herein may be manufactured, used, and licensed by or for the U.S. Government for governmental purposes without payment of any royalties thereon.

BACKGROUND

The publications and other materials referred to herein by author and date are incorporated herein by reference, and are listed alphabetically by author in the appended bibliography.

This application relates in general to fluid samplers and, in particular, to the automated collection of stormwater-quality samples in a vertical profile.

Sediment is a pollutant in rivers, streams, lakes, and reservoirs that can destroy aquatic habitats and affect our drinking water and recreational activities such as swimming. Many of today's environmental policies are oriented towards controlling the quantity of sediment and sediment-associated constituents from not only large rural watersheds but also smaller urban drainage basins into receiving waters. These policies are based upon scientific research designed to characterize and quantify the presence of a suite of regulated contaminants. Proper characterization depends on the collection, processing, and analysis of accurate concentration data.

Autosamplers are widely used to collect stormwater-quality samples where the remoteness or inaccessibility of a study site precludes manual collection. Additionally, autosamplers can be programmed to acquire samples in an environment that is rapidly changing, such as is the case when sampling urban runoff. The collection of a representative stormwater-quality sample in urban runoff can be difficult due to large sources of variability, both temporal and spatial (Selbig and Bannerman, 2007; Horowitz, 1995). Use of automated stormwater-quality samplers has vastly improved the way water resources professionals collect samples in these environments. However, these automated pumping systems do not always collect a representative aliquot of the flow moving past the sample intake, resulting in biased concentration data (Smith, 2002; Fowler et al., 2009).

SUMMARY

One of the sources of such non-representative samples is the settling of sediments in flows. A study conducted by the inventors collected and characterized data derived from stormwater-quality samples from urban basins. The intakes of autosamplers were located at different vertical locations in the water column, including approximately 1 inch off the pipe invert and at 30 and 60 percent of the water level. The inventors observed from the resulting sediment concentration and particle size distribution data that larger particles tend to concentrate near the bottom of the pipe. In general, concentrations of suspended sediment decreased with increasing vertical distance from the storm sewer invert. Similarly, median particle sizes also decreased with increasing distance from the pipe floor. As energy of flow increases with increasing discharge, stratification of sediment size and concentration become more apparent, suggesting vertical stratification of solids by particle size in the flowing water column of storm sewer runoff.

Typically, the intake orifice of an autosampler is located near the pipe floor to capture low flow conditions. The recommended intake orifice diameter for automated samplers is approximately ⅜-inch (Teledyne ISCO, 2008). Therefore, in large diameter pipes, the stormwater-quality sample collected by the autosampler represents only the bottom ⅜-inch of the pipe. During higher flows, the majority of the water column is not sampled. Even in circular pipes with a diameter as small as 1 foot, the concentration and distribution of sediment is concentrated near the bottom of the pipe over a range of flow conditions (Smith, 2002). Thus, resulting concentration data and particle size distributions using the suggested autosampler installation configurations could bias towards larger particles that tend to accumulate near the bottom of a pipe or other conveyance.

The ability of an autosampler to collect a representative stormwater-quality sample has relied upon proper mixing of the flow stream prior to sampling. This would disperse all sediment into a homogenous mixture rendering the location of sample acquisition in the water column irrelevant. However, the energy required to distribute coarse material homogenously throughout the water column is insufficient under normal flow conditions (Clark et al., 2008). Coarse particles with high specific density become stratified and tend to be transported along the bottom of the pipe floor. Attempts to artificially provide agitation in the flow path to produce a sample representing the average concentration of suspended sediment have proved unsatisfactory (Smith, 2002). Since introduction of objects in the flow path can often alter the hydrology by slowing down flow, and thus allowing sediment to settle out of suspension, most efforts for a homogenous runoff mixture are focused at a nearby outfall. However, site conditions or study requirements may preclude sampling at an outfall. Also, in an urban environment, the energy required to transport sediment in a pipe via increased flow can change rapidly such that sediment moving as bedload can quickly be carried as suspended load, and vice versa. Therefore, proper characterization of the distribution of particles in urban runoff requires the collection of water-quality samples from multiple, rather than a single fixed point in the water column.

In accordance with the invention, then, there is provided a liquid sampling method, assembly, and device to assist an autosampler in collecting stormwater-quality samples that are more representative of the entire water column. Stormwater-quality sampling in a pipe is traditionally done by installing a single sample tube at a fixed point near the bottom of a pipe. Described herein is an auxiliary sampling device for use with an autosampler that improves upon this concept by connecting the sample tube to the described device so that stormwater-quality samples can be acquired from a single or multiple points in the water column. Integrating data from multiple points spaced vertically throughout the water column, rather than using a single, fixed point, results in a more accurate representation of stormwater-borne solids.

In accordance with one embodiment of the invention, an auxiliary sampling device has a support frame with a pivot member at a first end of the support frame. A linear actuator is attached to a second end of the support frame opposite the pivot member. The linear actuator has a piston that extends towards the first end of the support frame. A rotatable sample arm assembly has an upper end attached to the piston and to the pivot member of the support frame, and a lower end with an inlet to receive a fluid sample. A fluid conduit extends through the sample arm assembly and has a fluid intake end connected to the inlet and a fluid discharge end connected to the autosampler. The linear actuator pushes or retracts the piston to vertically pivot the sample arm assembly until the inlet reaches desired positions within the fluid source so that the autosampler collects one or more samples at various depths.

In accordance with another embodiment, a method of collecting samples from a fluid source using an autosampler includes assembling an auxiliary sampling device by providing a support frame having a pivot member at a first end of the support frame; attaching a motorized piston to a second end of the support frame opposite the first end, the motorized piston having a piston that extends towards the first end of the support frame; providing a rotatable sample arm assembly having an upper end and a lower end with an inlet to receive a fluid sample, and attaching the upper end to the piston and to the pivot member of the support frame; and placing a fluid conduit, having a fluid intake end and a fluid discharge end, within the sample arm assembly, and connecting the fluid intake end to the inlet to receive the fluid sample and connecting the fluid discharge end to the autosampler. The motorized piston is controlled to push or retract the piston to vertically pivot the sample arm assembly to position the inlet at a desired level within the fluid source. Fluid is drawn, by the autosampler, up the fluid conduit to a storage container. The motorized piston is repeatedly controlled to position the inlet of the sample arm assembly at various levels within the fluid source to collect multiple samples.

In accordance with another embodiment, a fluid collection assembly includes an autosampler and an auxiliary sampling device. The auxiliary sampling device includes a support frame, a motorized piston, and a rotatable sample arm assembly. The support frame has a pivot member on one end. The motorized piston is attached to the other end of the support frame and has a piston that extends towards the pivot member. The rotatable sample arm assembly has an upper end attached to the piston and to the pivot member of the support frame, and a lower end with an inlet to receive a fluid sample. A fluid conduit extends through the sample arm assembly and has a fluid intake end connected to the inlet and a fluid discharge end connected to the autosampler. The linear actuator pushes or retracts the piston to vertically pivot the sample arm assembly until the inlet reaches desired positions within the fluid source so that the autosampler collects one or more samples at various depths.

Thus, the auxiliary sampling device described herein relates to the automated collection of stormwater-quality samples at one or more depths in a vertical profile. The collection of stormwater-quality samples at multiple depths provides a composite sample that is more representative of the entire water column.

BRIEF DESCRIPTION OF THE DRAWINGS

Various aspects and advantages of the invention will become apparent from the following detailed description, taken in conjunction with the accompanying drawings, of which.

DETAILED DESCRIPTION OF THE PREFERRED EMBODIMENTS

The general field of application of the liquid sampling method, assembly, and auxiliary sampling device described herein is intended to be in closed structures used to convey stormwater runoff in an urban environment, such as storm sewers, and embodiments of the invention will be described in this context. However, the invention may also be used in any water-quality sampling environment where the distribution of sediment in flow can be shown to be heterogeneous and not easily corrected using established manual sampling techniques (e.g., equal width increment sampling and equal depth increment sampling).

Figure 1:
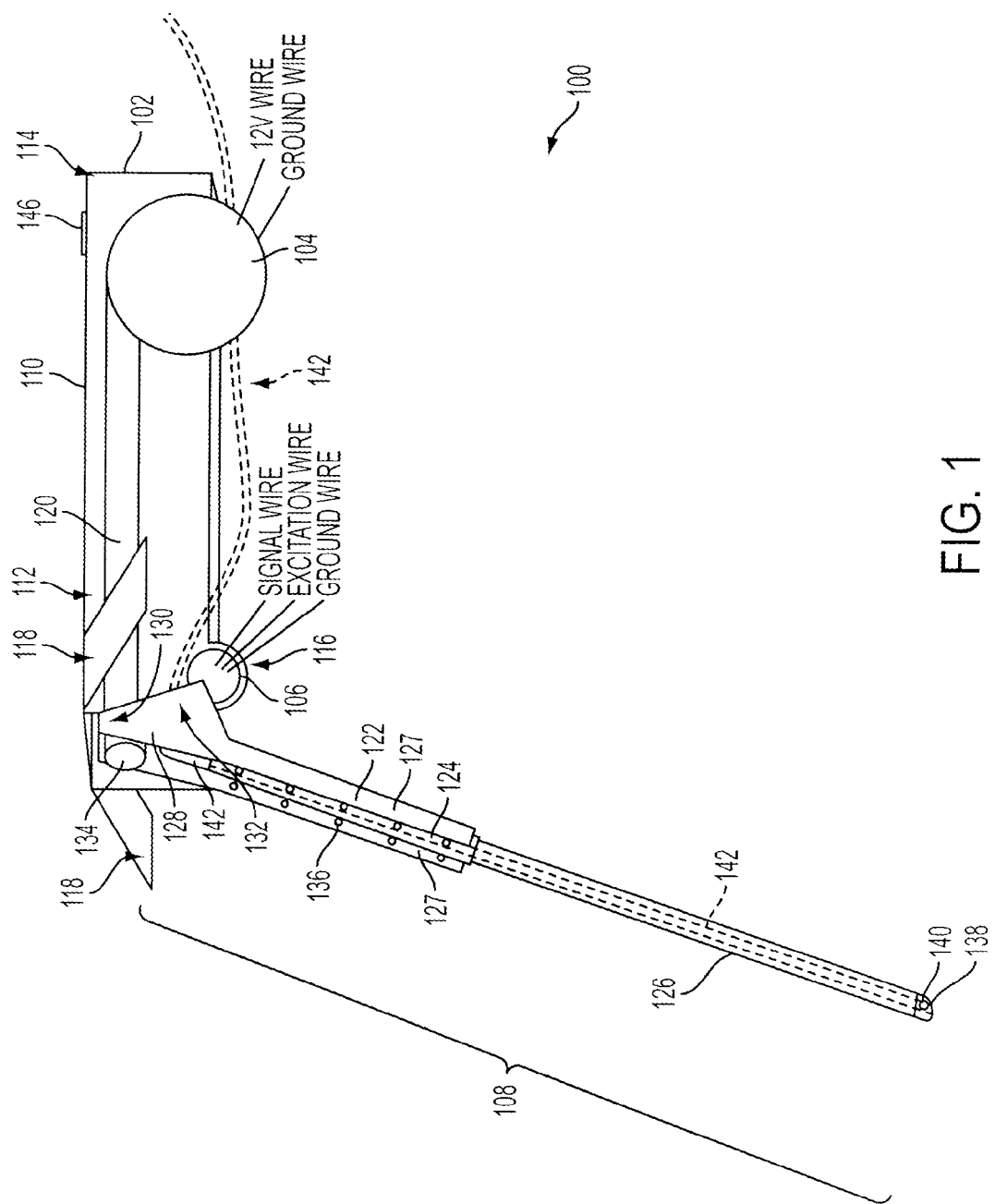
FIG. 1 shows a side view of an auxiliary sampling device embodying the principles of the invention in accordance with one embodiment of the invention.
Figure 2:
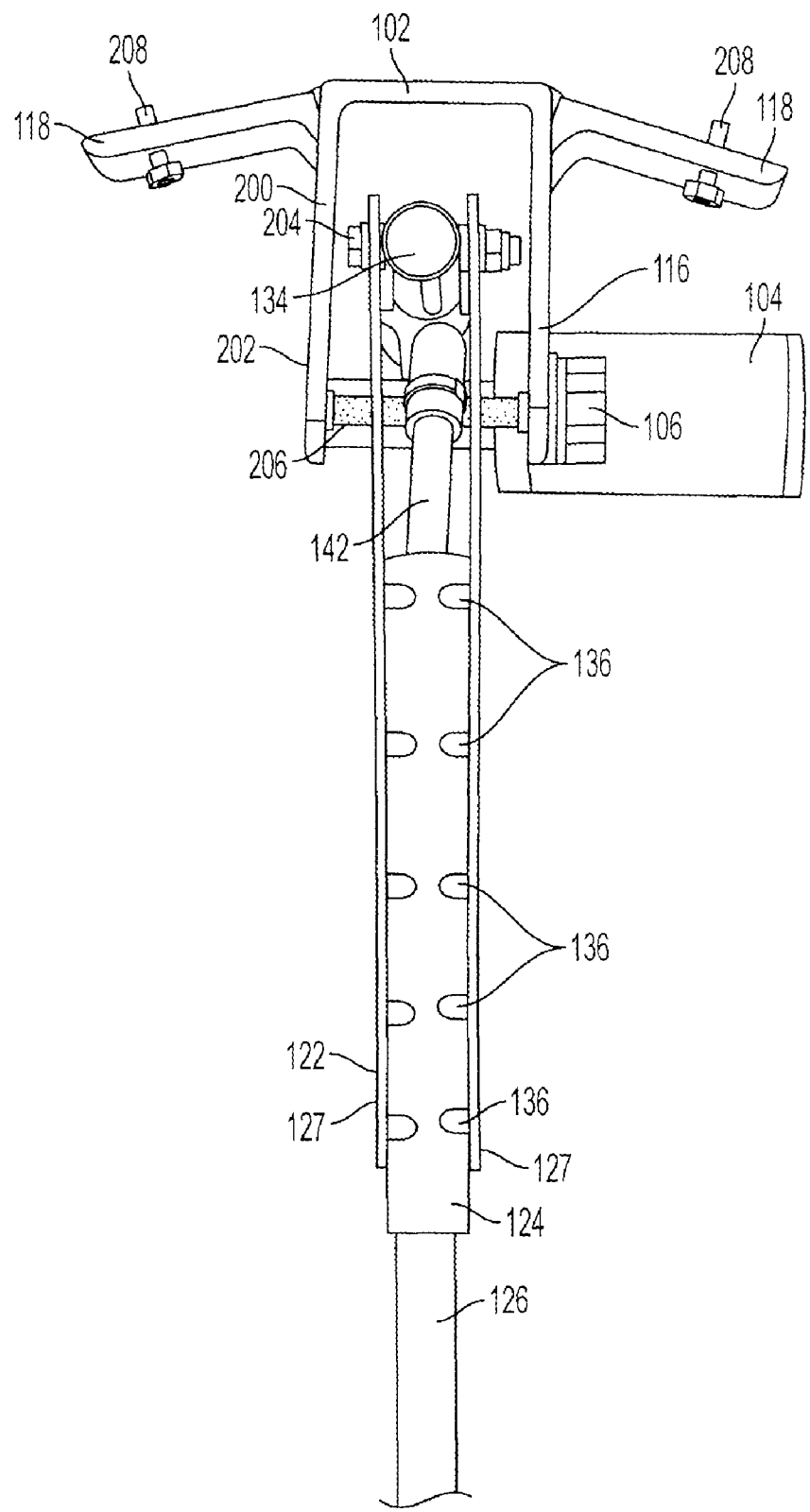
FIG. 2 shows a front view of the auxiliary sampling device of FIG. 1.
Figure 3:
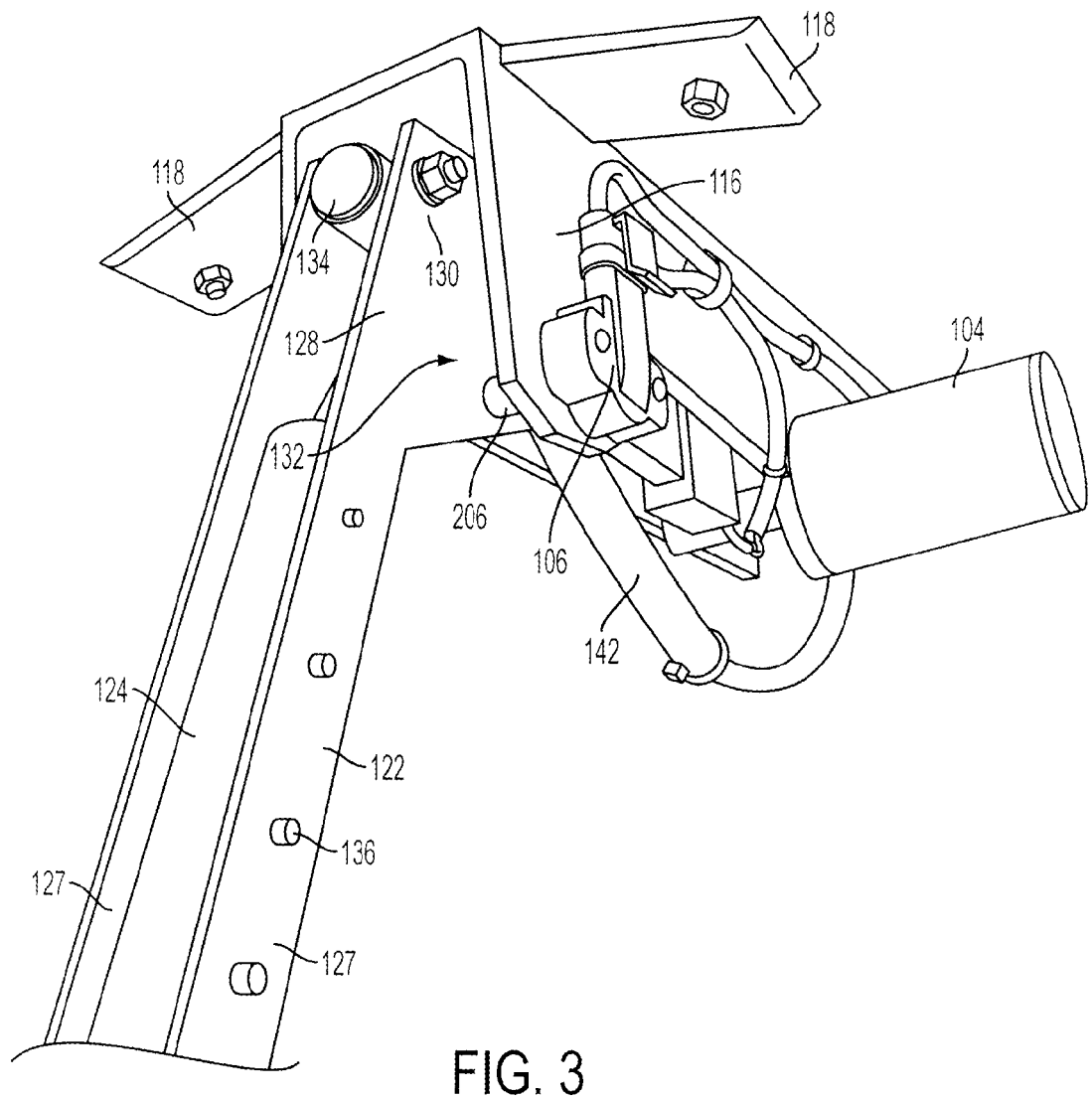
FIG. 3 shows a perspective view of the right side of the auxiliary sampling device of FIG. 1.
Figure 4:
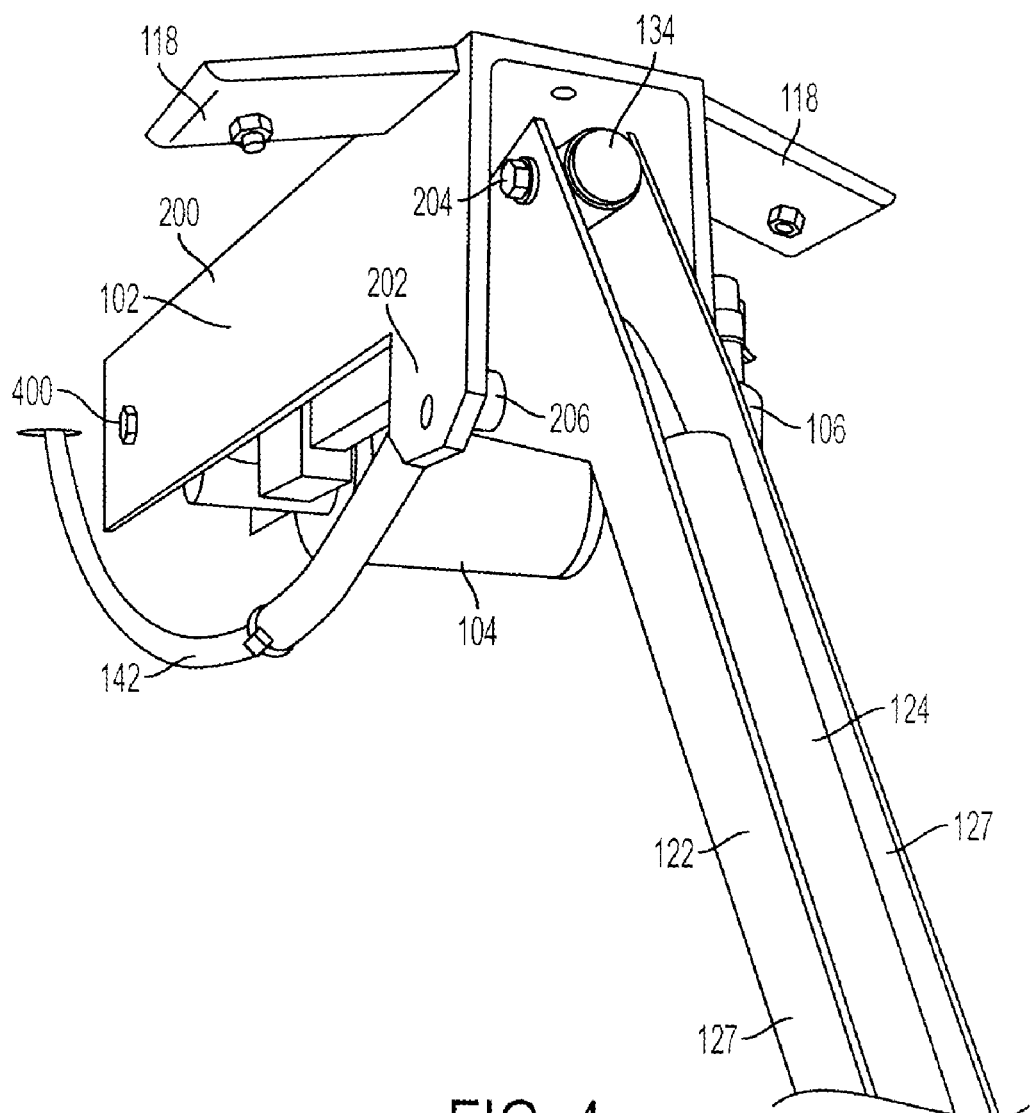
FIG. 4 shows a perspective view of the left side of the auxiliary sampling device of FIG. 1.

Referring to FIGS. 1 through 4, there is shown an exemplary auxiliary sampling device 100 of the present invention. FIG. 1 shows a side view of the auxiliary sampling device 100 in accordance with one embodiment of the invention. FIG. 2 shows a front view of the auxiliary sampling device 100. FIGS. 3 and 4 show right and left sides, respectively, of the auxiliary sampling device 100. The auxiliary sampling device 100 has a support frame 102, a motorized piston 104 (also referred to as a linear actuator or a ball drive actuator), a rotary potentiometer 106, and a sample arm assembly 108. The support frame 102, made of a material such as aluminum or stainless steel, has a top mounting plate 110 that is mounted to the ceiling or headwall of a storm sewer (such as storm sewer 800 illustrated in FIG. 8). The mounting plate 110 has a front portion 112 and a back portion 114. A side plate 200 (FIGS. 2 and 4) extends downward from the left side of the mounting plate 110. A first leg 202 extends downward from the side plate 200 at the front portion 112 of the mounting plate 110. A second leg 116 extends downward from the front portion 112 of the mounting plate 110 opposite the first leg 202 (FIGS. 1 and 3). Mounting brackets 118 project outward from the sides of the front portion 112 of the mounting plate 110.

The motorized piston 104, such as the 12 VDC motorized piston manufactured by Motion Systems Corporation, Eatontown, N.J., has a mounting eyelet (such as mounting eyelet 514 illustrated in FIGS. 5 and 6) for attachment to the support frame 102, and a piston 120 that it pushes or retracts, depending on DC voltage polarity. The piston 120 preferably has an extension length of about four inches. The motorized piston 104 is secured to the support frame 102 using a motorized piston mount 400 (FIG. 4) such as a threaded bolt that is inserted through the mounting eyelet 514 and secured to the side plate 200.

The sample arm assembly 108 includes a stabilizing channel 122, a housing 124, and a shaft 126. As shown in the embodiment of FIGS. 1 to 3, the stabilizing channel 122 is constructed of two elongated, flat metal plates, such as aluminum or stainless steel plates, that form the sides 127 of the stabilizing channel 122. Each side 127 of the stabilizing channel 122 has an upper member 128 with an upper end 130 and a flange 132 extending from the upper member 128. The upper end 130 of each upper member 128 is attached to a terminus 134 of the piston 120 by threading a piston mount 204 such as a threaded bolt (FIG. 2) through holes in each of the sides 127 of the stabilizing channel 122 and through a hole in the piston 120. Each flange 132 is attached to a potentiometer axle 206 (also referred to as a "pivot member"). The potentiometer axle 206 is supported on each end by the first leg 202 and the second leg 116 of the support frame 102 (FIGS. 2 to 4). One end of the potentiometer axle 206 is connected to the potentiometer 106. As the piston 120 extends or retracts, it pivots the stabilizing channel 122 around the potentiometer axle 206. This allows the potentiometer 106 to measure the rotational position of the stabilizing channel 122 as it pivots up or down. The potentiometer 106 may be scaled or calibrated to meet the parameters for each individual field setting. The full rotational range of the stabilizing channel 122 (and thus the sample arm assembly 108) is 90 degrees traveling from completely vertical to completely horizontal.

The housing 124 is attached to the inside of the stabilizing channel 122. In the embodiment shown in FIGS. 1 through 4, the housing 124 is a 1.5×0.625-inch elliptical, stainless steel housing that is welded to the stabilizing channel 122. The shaft 126 is inserted into the lower end of the housing 124 and secured in place with fasteners such as a series of set screws 136 that push the shaft 126 against the housing 124. In the embodiment shown in FIGS. 1 through 4, the shaft 126 is a 1.25×0.375-inch elliptical, stainless steel shaft. The shaft 126 may be adjusted up or down within the housing 124 by adjusting the set screws 136 so that the bottom end of the shaft 126 reaches the floor of the storm sewer 800.

At the terminus of the shaft 126 is an end cap 138 (FIG. 1), made of an inert material such as polycarbonate, with opposing intake orifices 140. The end cap 138 is secured to the shaft 126 by compression fitting. The intake orifices 140 are formed by drilling two holes on opposing sides of the end cap 138 so that flow moves parallel to each orifice opening. In the embodiment shown in FIG. 1, the intake orifices 140 are both 0.25-inch inner diameter (ID) holes. Water is drawn from the source through the intake orifices 140 into a sample tube 142 located inside the shaft 126. In the embodiment shown in FIG. 1, the sample tube 142 has a 0.375-inch inner diameter and is made of flexible polyethylene. The sample tube 142 is connected to the end cap 138 by insertion into a hole drilled in the top of the end cap 138. For example, a 0.5-inch outer diameter hole may be drilled in the top of the end cap 138 to receive the sample tube 142 having a 0.375-inch ID. The sample tube 142 and its connection to the end cap 138 are contained within the shaft 126. The sample tube 142 extends continuously from the end cap 138 up through the shaft 126 and the housing 124, over the potentiometer axle 206, and underneath the piston 120. The sample tube 142 is then routed to an autosampler (such as autosampler 802 illustrated in FIG. 8). The autosampler may be manufactured by Teledyne ISCO, Lincoln, Nebr., for example.

The support frame 102 is mounted to the ceiling of the storm sewer 800 (FIG. 8) using appropriate fasteners such as concrete anchors 208 (FIG. 2). The concrete anchors 208 hold the support frame 102 to the storm sewer 800 at the back portion 114 of the support frame 102 through a rear mounting hole 146 (FIG. 1) and at the front portion 112 of the support frame 102 through the mounting brackets 118.

Figure 5:
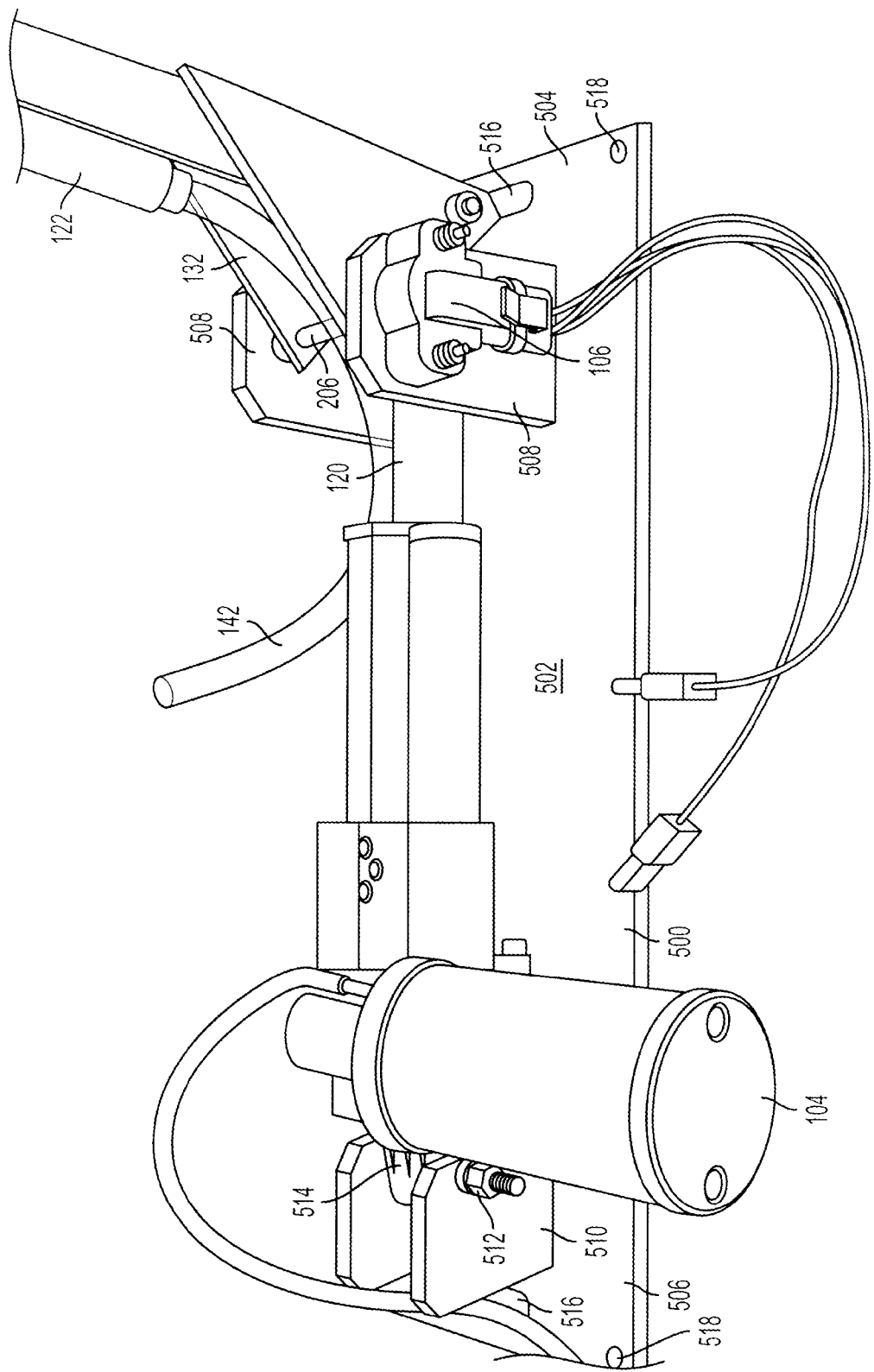
FIG. 5 shows a perspective view of an underside of a support frame in accordance with another embodiment of the invention.
Figure 6:
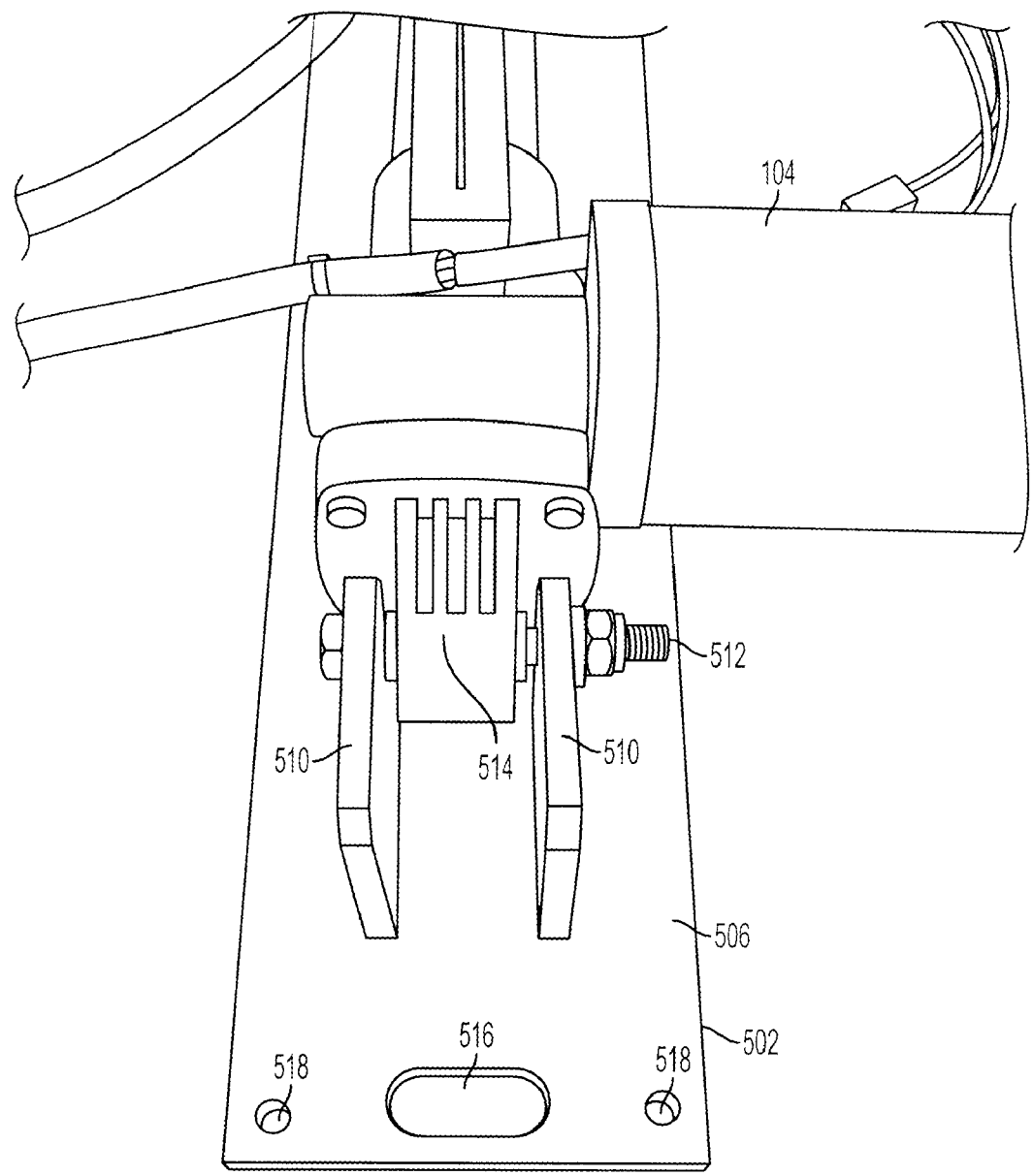
FIG. 6 shows a back portion of the underside of the support frame of FIG. 5.
Figure 7:
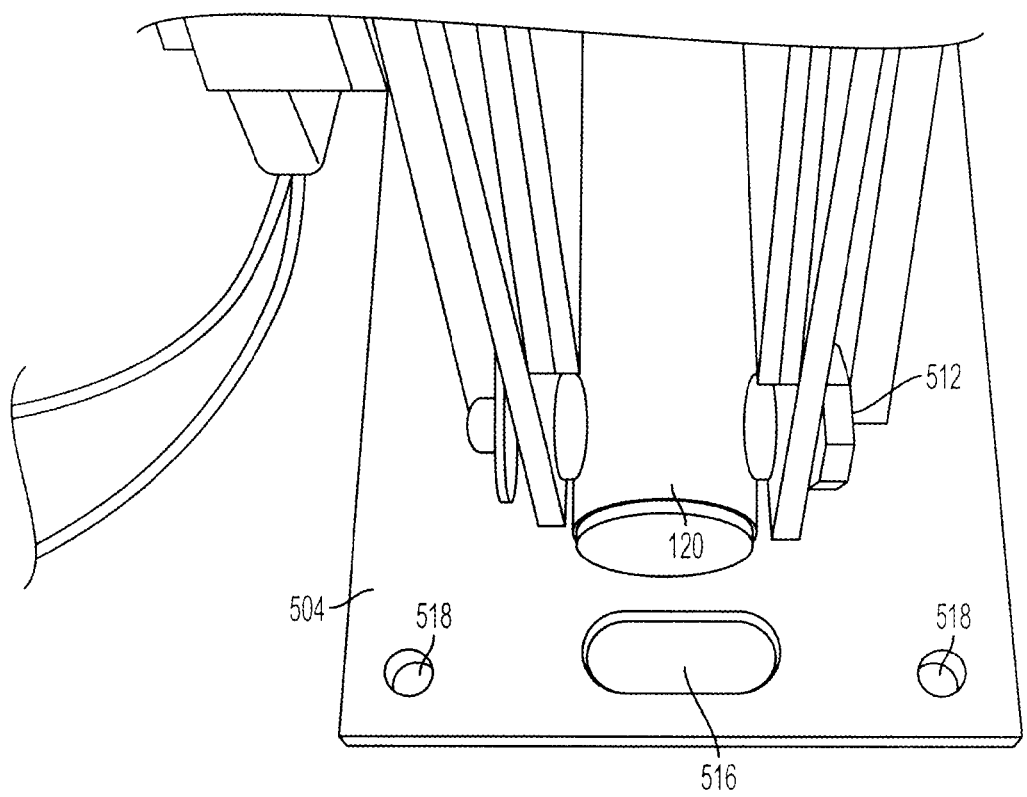
FIG. 7 shows a front portion of the underside of the support frame of FIG. 5.

FIG. 5 shows the underside of another support frame 500 according to an alternative embodiment. In the embodiment shown in FIG. 5, the support frame 500 has a mounting plate 502 with a front portion 504 and a back portion 506. Front legs 508 extend from the front portion 504 and back legs 510 extend from the back portion 506. The potentiometer axle 206 is supported on each end by the front legs 508 of the support frame 500. FIG. 6 shows the back portion 506 of the support frame 500, and FIG. 7 shows the front portion 504 of the support frame 500. As shown in FIG. 6, the motorized piston 104 is secured to the support frame 500 by threading a mounting bolt 512 through the back legs 510 and through the mounting eyelet 514. In this embodiment, the concrete anchors 208 hold the support frame 500 to the storm sewer 800 through center-line anchor slots 516 located at the front portion 504 (FIG. 7) and the back portion 506 (FIG. 6) of the mounting plate 502. The center-line anchor slots 516 allow the mounting plate 502 to be swiveled to the left or right a few centimeters to adjust the sample arm assembly 108 so that it is positioned in the center of the storm sewer 800. Once the support frame 500 is anchored to the ceiling of the storm sewer 800, it can be adjusted to a level position by inserting lateral-stabilizer bolts (not shown) through holes 518 located at each corner of the support frame 500, again to position the sample arm assembly 108 so that it is placed in the center of the storm sewer 800. The lateral-stabilizer bolts also act as stabilizers so that when the support frame 500 is positioned correctly, these bolts are threaded securely up against the ceiling of the storm sewer 800 at all four corners.

Figure 8:
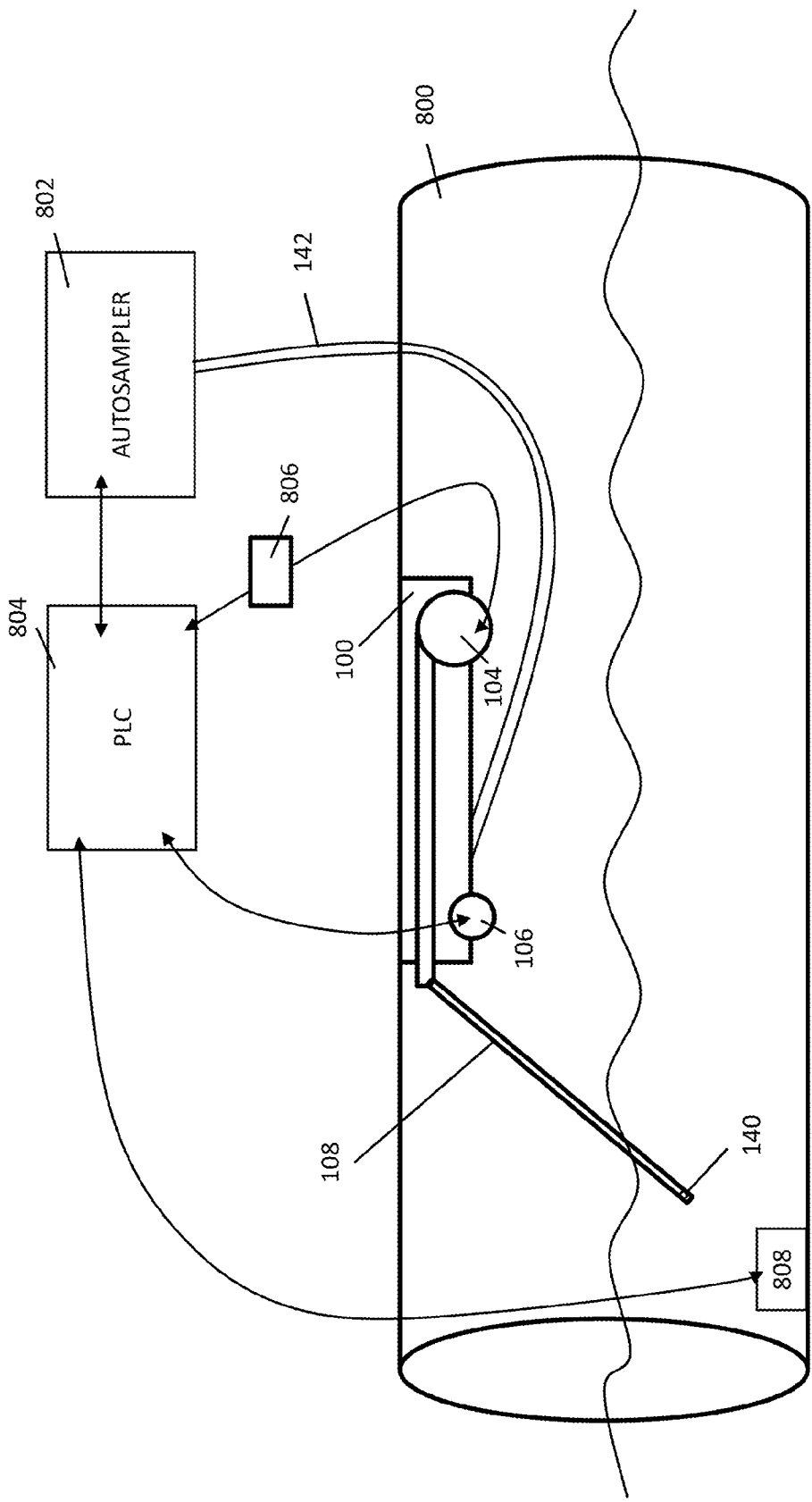
FIG. 8 shows a schematic representation of the auxiliary sampling device of FIG. 1 attached to the ceiling of a storm sewer.

FIG. 8 shows a general view of the auxiliary sampling device 100 within the storm sewer 800. The rotation of the sample assembly arm 108, and thus the position of the intake orifices 140, is controlled by an external datalogger or other programmable logic control (PLC) device 804, that activates a double-pole, double-throw relay 806 to energize the motorized piston 104. The PLC 804, the relay 806, and the autosampler 802 are located above ground in a weatherproof enclosure (not shown).

The PLC 804 may be programmed to set the intake orifices 140 to a percentage of the water depth. The vertical position of the intake orifices 140 is determined using a $5^{th}$-order polynomial scaled to represent water depth as a function of voltage. To calibrate the potentiometer 106 to site conditions, a user directs the potentiometer 106 to move to a target position manually. Once the sample arm assembly 108 has moved to that position, the depth of the intake orifices 140 above the floor of the storm sewer 800 is measured. This process is repeated for multiple target positions until a sufficient number of data points has been determined to develop a polynomial regression. Between five and ten data points are preferably determined.

The depth of water is measured by an acoustic-velocity sensor 808, or similar device. The acoustic velocity sensor 808, such as an acoustic velocity sensor manufactured by Teledyne ISCO, Lincoln, Nebr., is a low-profile sensor that is mounted to the floor of the storm sewer 800. An attached cable is routed up from the acoustic-velocity sensor 808 to the PLC 804. Upon initiation of a stormwater-quality sample, the PLC 804 uses the instantaneous water depth measured by the acoustic-velocity sensor 808 to compute a target voltage using the $5^{th}$-order polynomial. The PLC 804 then activates the motorized piston 104 to move the piston 120 forward or backward until the potentiometer 106 reaches the target voltage. For example, if the target sample position is set to be 50% of an actual water depth of 0.5 feet, then the PLC 804 will activate the motorized piston 104 until the potentiometer 106 reads the voltage representing 0.25 feet.

Thus, the motorized piston 104 rotates the sample arm assembly 108 to any vertical depth within the storm sewer 800. Once the PLC 804 determines that the potentiometer 106 has reached the target voltage, the PLC 804 controls the autosampler 802 to operate with normal purge/withdraw cycles to collect a stormwater-quality sample and deposit it in one or more storage containers. Once the sample has been acquired, the sample arm assembly 108 either moves to a new position for collection of another sample or fully retracts to the horizontal position, which removes the sample arm assembly 108 from the flow path. Any debris that may have accumulated on the sample arm assembly 108 while acquiring a sample is cleared away by water discharging past the sample arm assembly 108 as it retracts into the horizontal position.

As discussed above, the inventors have demonstrated that stormwater-quality samples collected from the lower, middle, and upper zones of flow in a storm sewer have sediment concentrations and particle sizes that are vertically stratified, decreasing with increasing distance from the pipe invert. Use of a fixed-point sample intake located near the bottom of a storm sewer can overestimate concentrations of suspended sediment since particles with a high specific density tend to travel along the pipe floor, especially in less turbulent flow, which is a condition commonly found in storm sewers. Limitations associated with fixed-point autosamplers can be overcome by positioning the sample intake orifice such that multiple aliquots are collected throughout the vertical profile of the water column. Integration of these zones into a single composite stormwater-quality sample can produce sediment and sediment-associated constituent concentrations that are more representative of the average condition. Additionally, securing the sample tubing along the pipe wall can create a barrier to flow, causing coarse particles to potentially settle out of suspension, thus causing a zone of sediment enrichment near the sample intake. This impediment is eliminated when using the auxiliary sampling device described herein since it has a small footprint in the flow path while temporarily collecting a sample before fully retracting back to the horizontal position.

From the description above, a number of advantages of the auxiliary sampling device become evident. These advantages include the following:

(a) the auxiliary sampling device allows sample acquisition from one or more points in the water column in a pipe;

(b) the auxiliary sampling device is fully retractable and self-cleaning, which reduces the potential of becoming fouled with debris;

(c) the auxiliary sampling device does not interfere with the natural hydrology of the conveyance because it is fully retractable to a horizontal position;

(d) the auxiliary sampling device is controllable via datalogger or other programming logic control device;

(e) the auxiliary sampling device does not rely on mixing of sediment in flow because samples are taken at multiple depths to provide a composite sample that is more representative of the entire water column; and (f) the auxiliary sampling device is scalable to fit a variety of pipe diameters or site specific conditions.

Accordingly, the auxiliary sampling device described herein provides for the collection of stormwater-quality samples from one or multiple points in the water column. The integration of samples from the entire water column, rather than from a single, fixed point, results in a more accurate representation of stormwater-borne solids.

Thus, it will be appreciated by those skilled in the art that modifications and variations of the present invention are possible without departing from the principles and spirit of the invention, the scope of which is defined in the appended claims and their equivalents.

LIST OF REFERENCE NUMERALS

- 100 auxiliary sampling device
- 102 support frame of a first embodiment
- 104 motorized piston
- 106 potentiometer
- 108 sample arm assembly
- 110 mounting plate of support frame of first embodiment
- 112 front portion of mounting plate of first embodiment
- 114 back portion of mounting plate of first embodiment
- 116 second leg of support frame of first embodiment
- 118 mounting brackets
- 120 piston
- 122 stabilizing channel
- 124 housing
- 126 shaft
- 127 stabilizing channel side plates
- 128 upper member of stabilizing channel
- 130 upper end of upper member of stabilizing channel
- 132 flange extending from upper member of stabilizing channel
- 134 terminus of piston
- 136 set screws
- 138 end cap
- 140 intake orifices
- 142 sample tube
- 146 rear mounting hole
- 200 side plate of support frame of first embodiment
- 202 first leg of support frame of first embodiment
- 204 piston mount
- 206 potentiometer axle
- 208 concrete anchors
- 400 motorized piston mount
- 500 support frame of a second embodiment
- 502 mounting plate of support frame of second embodiment
- 504 front portion of support frame of second embodiment
- 506 back portion of support frame of second embodiment
- 508 front legs of support frame of second embodiment
- 510 back legs of support frame of second embodiment
- 512 mounting bolt securing motorized piston mount to support frame of second embodiment
- 514 mounting eyelet of motorized piston
- 516 center-line anchor slots on support frame of second embodiment
- 518 holes for lateral-stabilizer bolts on support frame of second embodiment
- 800 storm sewer
- 802 autosampler
- 804 programmable logic control (PLC) device
- 806 relay
- 808 acoustic velocity sensor

GENERAL BIBLIOGRAPHY ON THE SUBJECT

The following bibliography provides citations to the references cited in the above text. The references are provided merely to clarify the description of the present invention and citation of a reference either in the bibliography below or in the specification above is not an admission that any such reference is "prior art" to the invention described herein.

1. Clark, S. E., Siu, C. Y. S., Pitt, R., Roenning, C. D., and Treese, D. P., 2008, Peristaltic pump autosamplers for solids measurement in stormwater runoff, Water Environment Research, v. 80, 9 p.
2. Fowler, G. D., Roseen, R. M., Ballestero, T. P., Guo, Q., and Houle, J., 2009, Sediment monitoring by autosampler in comparison with whole volume sampling for parking lot runoff, ASCE Conf. Proc. 342, 150 (2009).
3. Horowitz, A. J., 1995, The use of suspended sediment and associated trace elements in water quality studies, International Association of Hydrological Sciences Special Publication No 4, 58 p.
4. Selbig, W. R. and Bannerman, R. T., 2007, Evaluation of street sweeping as a stormwater-quality management tool in three residential basins in Madison, Wis., U.S. Geological Survey Scientific Investigations Report 2007-5156, 120 p.
5. Smith, K. P., 2002, Effectiveness of three best management practices for highway-runoff quality along the southeast expressway, Boston, Mass., U.S. Geological Survey Water-Resources Investigations Report 02-4059, 62 p.
6. Teledyne ISCO, 2008, 3700R/3740 refrigerated sampler instruction manual, accessed Dec. 16, 2009, at URL http://www.isco.com/pcfiles/Part PDF3/UP000XKF.pdf.

What is claimed is:

1. An auxiliary sampling device to assist an autosampler in collecting samples from a fluid source, comprising:
    a support frame having a pivot member on an end thereof;
    a linear actuator, having a piston, attached to an end of the support frame opposite the pivot member;
    a rotatable sample arm assembly having an upper end attached to a terminus of the piston and to the pivot member and having a lower end with an inlet to receive a fluid sample; and
    a fluid conduit within the sample arm assembly having a fluid intake end connected to the inlet and a fluid discharge end connected to the autosampler,
    wherein the linear actuator pushes or retracts the piston to vertically pivot the sample arm assembly until the inlet reaches desired positions within the fluid source so that the autosampler collects multiple samples at various depths.

2. The auxiliary sampling device of claim 1, wherein the linear actuator is a 12 VDC motorized piston.

3. The auxiliary sampling device of claim 1, wherein the sample tube is made of flexible polyethylene.

4. The auxiliary sampling device of claim 1, further comprising a rotation sensor attached to the pivot member to measure the rotational position of the sample arm assembly as the piston extends or retracts.

5. The auxiliary sampling device of claim 4, wherein the rotation sensor is a rotary potentiometer.

6. The auxiliary sampling device of claim 1, wherein the sample arm assembly further comprises a stabilizing channel having an upper member with an upper end and a projection extending from the upper member, the upper end of the upper member being attached to the terminus of the piston and the projection being attached to the pivot member, the projection rotating around the pivot member as the piston extends or retracts.

7. The auxiliary sampling device of claim 6, wherein the stabilizing channel and the support frame are made of aluminum or stainless steel.

8. The auxiliary sampling device of claim 6, wherein the sample arm assembly further comprises:
    an elongated shaft having a tube shape with an upper end and a lower end;
    a housing having a tube shape and being attached to an inside of the stabilizing channel to surround the upper end of the shaft, the upper end of the shaft being received by a bottom end of the housing, and a length of the sample arm assembly being adjustable by varying the distance the upper end of the shaft is inserted into the housing; and
    an endcap attached to the lower end of the shaft and having intake orifices that define the inlet.

9. The auxiliary sampling device of claim 8, wherein the intake orifices are formed on opposing sides of the endcap and are positioned so that the fluid from the fluid source moves parallel to each intake orifice, and a bottom end of the fluid conduit is connected to the endcap and receives the sample fluid through the intake orifices.

10. The auxiliary sampling device of claim 8, wherein the fluid intake end of the fluid conduit is connected to the endcap and receives the sample fluid through the intake orifices, and the fluid conduit extends from the endcap, through the shaft and the housing, to the autosampler.

11. The auxiliary sampling device of claim 8, wherein the endcap is made of an inert substance.

12. The auxiliary sampling device of claim 8, wherein the housing and the shaft are made of stainless steel.

13. The auxiliary sampling device of claim 1, wherein the sample arm assembly has a rotation range of about 90 degrees from a horizontal position to a vertical position to position the inlet at various depths.

14. The auxiliary sampling device of claim 13, wherein the sample arm assembly retracts to a horizontal position after sampling is completed to move the sample arm assembly from a flow path of the fluid source.

15. The sample device of claim 14, wherein the sample arm assembly self-cleans as it retracts to the horizontal position by fluid discharging past the sample arm assembly.

16. A method of collecting samples from a fluid source using an autosampler, comprising:
    assembling an auxiliary sampling device, comprising,
        providing a support frame having a pivot member on an end thereof,
        attaching a linear actuator with a piston to an end of the support frame opposite the pivot member,
        providing a rotatable sample arm assembly having an upper end and a lower end with an inlet to receive a fluid sample, and attaching the upper end to a terminus of the piston and to the pivot member of the support frame, and
        placing a fluid conduit, having a fluid intake end and a fluid discharge end, within the sample arm assembly, and connecting the fluid intake end to the inlet to receive the fluid sample and connecting the fluid discharge end to the autosampler;
    controlling the linear actuator to push or retract the piston, which vertically pivots the sample arm assembly to position the inlet at a desired level within the fluid source;
    drawing fluid up the fluid conduit to the autosampler; and
    repeatedly controlling the linear actuator to position the inlet of the sample arm assembly at various levels within the fluid source to collect multiple samples.

17. The method of claim 16, further comprising mounting the support frame of the auxiliary sampling device to a ceiling of a storm sewer and rotating the sample arm assembly downward from a horizontal position into the fluid source within the storm sewer to collect the samples.

18. The method of claim 17, further comprising controlling the linear actuator to retract the sample arm assembly to a horizontal position after sampling is completed to move the sample arm assembly from a flow path of the fluid source.

19. A fluid collection assembly, comprising:

an autosampler; and an auxiliary sampling device, comprising, a support frame having a pivot member on an end thereof, a linear actuator, having a piston, attached to an end of the support frame opposite the pivot member, a rotatable sample arm assembly having an upper end attached to a terminus of the piston and to the pivot member of the support frame and having a lower end with an inlet to receive a fluid sample, and a fluid conduit within the sample arm assembly having a fluid intake end connected to the inlet and a fluid discharge end connected to the autosampler, wherein the linear actuator pushes or retracts the piston to vertically pivot the sample arm assembly until the inlet reaches desired positions within the fluid source so that the autosampler collects multiple samples at various depths.

20. The fluid collection assembly of claim 19, further comprising:

a controller to control the linear actuator to rotate the sample arm assembly to position the inlet within the fluid source, and to control operation of the autosampler to draw the fluid through the fluid conduit and into a storage container; and a rotation sensor to measure the rotational position of the sample arm assembly.

21. The fluid collection assembly of claim 20, wherein the controller controls the linear actuator to rotate the sample arm assembly until the inlet is positioned at a predetermined percentage of the depth of the fluid source.

22. The fluid collection assembly of claim 20, further comprising a fluid level sensor to measure a depth of the fluid source and communicate same to the controller.

23. The fluid collection assembly of claim 22, wherein the controller receives the fluid depth measurement from the fluid level sensor, determines a voltage representing the fluid depth and a target voltage representing a target depth, and activates the linear actuator to extend or retract the piston, the sample arm assembly rotating around the pivot member until the rotation sensor reaches the target voltage.

\* \* \* \* \*